United States Patent [19]

Barber, Jr. et al.

[11] 3,962,346

[45] June 8, 1976

[54] 1,1-BIS(PERFLUOROALKYLSULFONYL)ETHENES

[75] Inventors: Loren L. Barber, Jr., Woodbury; Robert J. Koshar, Mahtomedi, both of Minn.

[73] Assignee: Minnesota Mining and Manufacturing Company, St. Paul, Minn.

[22] Filed: Mar. 7, 1975

[21] Appl. No.: 556,475

[52] U.S. Cl. .................. 260/607 A; 260/294.8 R; 260/583 EE
[51] Int. Cl.² ........................................ C07C 147/02
[58] Field of Search ........................... 260/607 AL

[56] References Cited
UNITED STATES PATENTS

| | | | |
|---|---|---|---|
| 2,641,594 | 6/1953 | Burney | 260/607 AL |
| 3,700,737 | 10/1972 | Mitsch et al | 260/607 AL |
| 3,758,591 | 9/1973 | Koshar | 260/607 AL |
| 3,758,592 | 9/1973 | Koshar | 260/607 AL |
| 3,758,593 | 9/1973 | Koshar | 260/607 AL |

*Primary Examiner*—Lewis Gotts
*Assistant Examiner*—D. R. Phillips
*Attorney, Agent, or Firm*—Alexander, Sell, Steldt & DeLaHunt

[57] ABSTRACT

Bis(perfluoroalkylsulfonyl)methanes condense with formaldehyde to give highly reactive 1,1-bis(perfluoroalkylsulfonyl)ethenes which are useful as catalysts for epoxy resins.

4 Claims, No Drawings

1,1-BIS(PERFLUOROALKYLSULFONYL)ETHENES

This invention relates to 1,1-bis(perfluoroalkylsulfonyl)-ethenes, and to the process for making and purifying them.

In copending application, Ser. No. 300,754, filed Oct. 25, 1972, there is described the reaction of various aldehydes with bis(perfluoroalkylsulfonyl)methanes. The series is commonly considered to begin with acetaldehyde because of the numerous reactions in which formaldehyde reacts differently from acetaldehyde and higher aldehydes. In this reaction, acetaldehyde itself reacts in an unexpected manner:

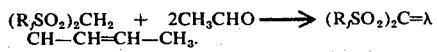

There is a continual need for catalysts for the polymerization of epoxy resins and particularly for catalysts having some selectivity in catalytic activity such as to polymerize aromatic epoxy resins rapidly at ambient conditions. It is well known that aromatic epoxy resins, e.g., derived from bisphenol A, are more difficult to polymerize than cycloaliphatic epoxy resins.

It is an object of this invention to provide new catalysts for the polymerization of aromatic epoxy resins. Other objects will become evident hereinelsewhere.

It is found that a series of new catalysts for polymerization of epoxy resins is obtained by condensation of formaldehyde or a precursor thereof with a bis(perfluoroalkylsulfonyl)methane. These compounds have the general formula

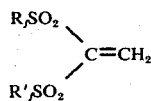

wherein $R_f$ and $R'_f$ are perfluoroalkyl radicals having 1–18 carbon atoms and preferably 1–8 carbon atoms. These novel compounds of the invention are found to be useful to catalyze the polymeization of epoxy compositions and are particularly useful in their ability to catalyze the polymerization of aromatic glycidyl ethers. These compounds of the invention are also found to have the unexpected property, not shown by compounds in which one of the vinyl hydrogens is replaced, of forming stable tertiary amine dipolar complexes which are useful for the purification of the compounds of the invention so that catalytic concentrations are more easily ascertained. This invention also relates to a process for making the 1,1-bis(perfluoroalkylsulfonyl)ethenes.

1,1-Bis(perfluoroalkylsulfonyl)ethenes are prepared by reaction of formaldehyde or preferably a formaldehyde precursor such as paraformaldehyde with bis(perfluoroalkylsulfonyl)methanes in an inert solvent.

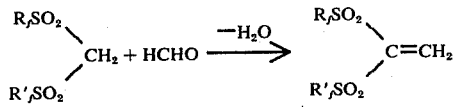

The reaction is carried out at 10° to 100° C. or higher, preferably at the reflux temperature of the solvent. Generally 0.7 to 2.0 mole of formaldehyde are used per mole of bis(perfluoroalkylsulfonyl)methane. Equimolar amounts of the two reactants are preferred. Inert solvents having low water solubility are used and water azeotroping solvents are preferred. Examples of such solvents include benzene, chlorobenzene, methylene chloride and 1,2-dichloroethane. Water produced in the process is removed, e.g., by azeotropic distillation, phase separator after completion of the reaction or use of suitable neutral drying agents as magnesium or calcium sulfates. The compounds of the invention are isolated by distillation or recrystallization. Compounds of the invention react with water to produce tetrasulfones, e.g.,

Although gaseous formaldehyde or formaldehyde solutions can be used in the process, formaldehyde polymers such as paraformaldehyde which liberate formaldehyde during the process are preferred because of convenience and ease of handling. $R_f$ and $R'_f$ are the same or different perfluoroalkyl groups which may be straight or branched chain. Compounds having a single hydrogen or chlorine in place of a terminal fluorine atom will be obvious equivalents. Examples of radicals which fall within the scope of this invention are perfluoromethyl (i.e., trifluoromethyl), perfluorododecyl, chloroperfluoromethyl, chloroperfluoroethyl, omega-chloroperfluorobutyl, perfluoroisopropyl, omega-hydroperfluoroethyl, omega-hydroperfluorobutyl and the like.

The starting bis(perfluoroalkylsulfonyl)methanes are prepared by procedures described in U.S. Pat. Nos. 3,776,960 and 3,704,311.

In addition to being catalysts for the polymerization of epoxy resins themselves, the 1,1-bis(perfluoroalkylsulfonyl)-ethenes of the invention are valuable intermediates for the formation of other active catalysts for the polymerization of epoxy resins. The reaction as an intermediate is illustrated by the addition of diethyl malonate to 1,1-bis(trifluoromethylsulfonyl)ethene to give

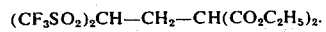

These reactions and the product are described and claimed in our copending application, Ser. No. 556,494, filed of even date herewith.

The following examples illustrate the details of preparing representative compounds of the invention. Temperatures are in degrees Centigrade and pressures are in mm. of mercury.

EXAMPLE 1

A mixture of 56 g. of bis(trifluoromethylsulfonyl)methane, 6 g. of paraformaldehyde and 150 ml. of benzene is heated under reflux until production of water ceases. Distillation affords 54 g. of distillate bp mainly at 88°–90° at 15 mm. which contains 66 mol. % $(CF_3SO_2)_2C{=}CH_2$ contaminated with $(CF_3SO_2)_2CHCH_3$.

EXAMPLE 2

This example illustrates the separation of high purity $(CF_3SO_2)_2C{=}CH_2$ from $(CF_3SO_2)_2CHCH_3$ using organic tertiary amines.

The procedure of Example 1 is repeated using 12 g. of paraformaldehyde instead of 6 g. Distillation yields 48 g. of distillate, boiling mainly at 89°–91° at 15 mm., containing 42 mol. % of $(CF_3SO_2)_2C=CH_2$ and 58 mol. % of $(CF_3SO_2)_2CHCH_3$.

To a solution of 16.6 g. of the above mixture in 40 ml. of 1,2-dichloroethane at room temperature is added 5.5 ml. of anhydrous pyridine. A precipitate is formed which is collected by filtration. The product is 10.1 g. of thermally stable white solid, m.p. 167°–169°, which is soluble and stable in hot water and has the novel zwitterionic structure:

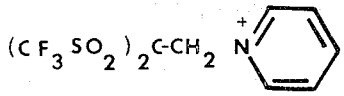

The $(CF_3SO_2)_2CHCH_3$ forms a salt with pyridine which is soluble in the filtrate.

Analysis: Calculated for $C_9H_7F_6S_2O_4N$: 29.2%, C; 30.7%, F; 3.8%, N. Found: 29.1%, C; 30.6%, F; 3.7% N.

A stable dipolar complex is also formed in a similar fashion when triethylamine and other tertiary and trialkyl amines of relatively low molecular weight are used instead of pyridine. In general, it is preferred that the molecule contain no more than about 12 carbon atoms and one tertiary nitrogen atom.

A mixture of 10 g. of the above pyridinium dipolar complex and 10 ml. of conc. sulfuric acid is stirred at 25° for 1 hour. Distillation gives 8.2 g. of high purity $(CF_3SO_2)_2C=CH_2$, bp 80° at 14 mm. Proton nuclear magnetic resonance spectroscopy shows a sharp singlet peak at 2.13 τ in deuterated chloroform. The ethylenic double bond absorbs at 6.27 μ.

Analysis: Calculated for $C_4H_2F_6O_4S_2$: 16.4%, C; 0.7%, H; 39.0%, F. Found: 16.4%, C; 0.7%, H; 38.0% F.

EXAMPLE 3

This example illustrates the use of $(CF_3SO_2)_2C=CH_2$ as a catalyst for the room temperature polymerization of aromatic glycidyl ethers (epoxy resins).

About 0.15 g. of high purity $(CF_3SO_2)_2C=CH_2$ is rapidly mixed with 3 g. of diglycidyl ether of bisphenol A (Epon 828) in an aluminum dish at room temperature. Considerable gel formation occurs after 15 seconds. After 5 minutes, the mixture is extremely difficult to stir and after 15 minutes, a hard solid polymer results. U.S. Pat. No. 3,632,843 discloses that use as a catalyst of $(CF_3SO_2)_2CH_2$ at a concentration of about 0.1 g. per 3 g. of Epon 828 gives no appreciable polymerization after 15 minutes at room temperature and a hard polymer only after heating to 80°.

EXAMPLE 4

Polymerizations are effected under ambient conditions using 1,1-bis(trifluoromethylsulfonyl)ethene at various concentrations in a resin mixture composed of 80 parts bisphenol A bisglycidyl ether (DER 331 of Dow Chemical Company) and 20 parts of Epotuf 37-123 (product of Reichhold Chemicals Inc. and believed to be a mixture of bisphenol A bisglycidyl ether and an aromatic glycidyl ether possibly of t-butyl phenol). Gel times are determined on a Sunshine Gel Time Meter (available from Sunshine Scientific Instrument Co., Philadelphia, Pa). The data are tabulated in Table 1.

Table 1

| Catalyst % wt. | Concentration millimoles per 100 g. resin | Gel Time minutes |
| --- | --- | --- |
| 0.6 | 2.1 | 19.8 |
| 0.7 | 2.4 | 11.1 |
| 0.8 | 2.7 | 7.9 |
| 0.9 | 3.1 | 2.5 |

EXAMPLE 5

A mixture of 4.0 g. of $(C_4F_9SO_2)_2CH_2$ (containing mainly linear but some branched $C_4F_9$ groups), 30 ml. of chlorobenzene and 0.42 g. of paraformaldehyde is stirred at 80° for two hours and under reflux for 6 hours; water is removed azeotropically and collected in a Dean-Stark water receiver. Filtration of the mixture gives 3.2 g. of white solid, m.p. 66°–85° containing 70 mol. % $(C_4F_9SO_2)_2C=CH_2$ and 30 mol. % of $(C_4F_9SO_2)_2CHCH_3$ as a by product. The ethylene exhibits a characteristic C=C infrared absorption at 6.32 microns and a proton n.m.r. singlet at 2.16 τ (deuterated chloroform as solvent). Recrystallization from $CCl_4$ gives a pure sample, m.p. 96°–97.5°.

Analysis: Calculated for $C_{10}H_2F_{18}O_4S_2$: 20.3%, C; 0.3%, H. Found: 20.2%, C; 0.5%, H.

When the above product mixture is reacted with pyridine as described in Example 2 above, separation or at least enrichment of the ethylene is effected as described in that example.

EXAMPLE 6

The procedure of Example 4 is repeated using a mixture of 10 g. of $(C_8F_{17}SO_2)_2CH_2$ (m.p. 161°–166°; containing mainly linear but some branched $C_8F_{17}$ groups), 30 ml. chlorobenzene and 0.45 g. of paraformaldehyde which is stirred under reflux for 6 hours removing water azeotropically. Filtration gives 9.0 g. of white solid which is washed with methylene chloride. About one gram of this solid is stirred with 30 ml. of $CF_2ClCFCl_2$ (Freon 113) and the mixture filtered. Evaporation of the filtrate gives 0.2 g. of $(C_8F_{17}SO_2)_2C=CH_2$, m.p. 145°–148° identified by infrared and n.m.r. analysis. This product shows the characteristic infrared absorption band at 6.30 microns of an ethylenic double bond and a singlet proton nuclear magnetic resonance peak at 2.36 τ ($CF_2ClCFCl_2$ as solvent).

Analysis: Calculated for $C_{18}H_2F_{34}O_4S_2$: 21.8%, C; 0.2%, H; 65.1%, F. Found: 21.6%, C; 0.3%, H; 64.1%, F.

What is claimed is:

1. A 1,1-bis(perfluoroalkylsulfonyl)ethene of the formula

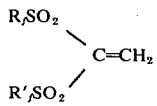

wherein $R_f$ and $R'_f$ are perfluoroalkyl radicals having 1–18 carbon atoms.

2. 1,1-Bis(trifluoromethylsulfonyl)ethene of the formula $(CF_3SO_2)_2C=CH_2$.

3. 1,1-Bis(perfluorobutylsulfonyl)ethene of the formula $(C_4F_9SO_2)_2C=CH_2$.

4. 1,1-Bis(perfluorooctylsulfonyl)ethene of the formula $(C_8F_{17}SO_2)_2C=CH_2$.

* * * * *

UNITED STATES PATENT AND TRADEMARK OFFICE
CERTIFICATE OF CORRECTION

PATENT NO. : 3,962,346

DATED : June 8, 1976

INVENTOR(S) : Barber, Jr. et al.

It is certified that error appears in the above—identified patent and that said Letters Patent are hereby corrected as shown below:

Column 1, line 16, "$\lambda$" should be deleted and the formula should be continued on the next line.

Column 1, line 44, "polymeization" should read -- polymerization -- .

Column 3, line 18, the hyphen between C and $CH_2$ ($C-CH_2$) should be a minus sign placed above the first C as ($\bar{C}CH_2$).

*Signed and Sealed this*

*Nineteenth* Day *of* October 1976

[SEAL]

Attest:

RUTH C. MASON
*Attesting Officer*

C. MARSHALL DANN
*Commissioner of Patents and Trademarks*